United States Patent [19]

Schliekelmann

[11] Patent Number: 4,507,967
[45] Date of Patent: Apr. 2, 1985

[54] METHOD AND APPARATUS FOR THE NON-DESTRUCTIVE TESTING OF MATERIALS BY THE USE OF ULTRA-SONIC WAVES

[75] Inventor: Robert J. Schliekelmann, Amstelveen, Netherlands

[73] Assignee: Fokker BV, Schiphol-Oost, Netherlands

[21] Appl. No.: 467,136

[22] Filed: Feb. 16, 1983

[30] Foreign Application Priority Data

Feb. 16, 1982 [NL] Netherlands .................. 8200589

[51] Int. Cl.³ ............................................ G01N 29/00
[52] U.S. Cl. ........................................ 73/621; 73/625; 73/628; 73/641
[58] Field of Search ................ 73/621, 624, 625, 626, 73/628, 633, 641

[56] References Cited

U.S. PATENT DOCUMENTS

| | | | |
|---|---|---|---|
| 3,938,371 | 2/1976 | Dini | 73/633 |
| 3,938,372 | 2/1976 | Sproule | 73/633 |
| 3,990,300 | 11/1976 | Kossoff | 73/621 |
| 4,038,865 | 8/1977 | Flambard et al. | 73/633 |
| 4,103,677 | 8/1978 | Lansiart et al. | 73/621 |
| 4,163,394 | 8/1979 | Soldner | 73/626 |
| 4,281,550 | 8/1981 | Erikson | 73/626 |
| 4,339,952 | 7/1982 | Foster | 73/624 |
| 4,341,120 | 7/1982 | Anderson | 73/621 |

FOREIGN PATENT DOCUMENTS

| | | | |
|---|---|---|---|
| 41664 | 12/1981 | European Pat. Off. | 73/625 |
| 2643126 | 3/1977 | Fed. Rep. of Germany | 73/625 |

*Primary Examiner*—Howard A. Birmiel
*Attorney, Agent, or Firm*—Handal & Morofsky

[57] ABSTRACT

A method for non-destructive, qualitative testing of properties of materials, whereby ultra-sonic waves are transmitted in the direction of the material. Ultra-sonic waves reflected by the material are received. The orientation of the material relative to the direction in which the ultra-sonic waves are transmitted is changed in a predetermined way, such that the transmitted ultra-sonic waves arrive at the material under varying angles of incidence and from different directions.

5 Claims, 3 Drawing Figures

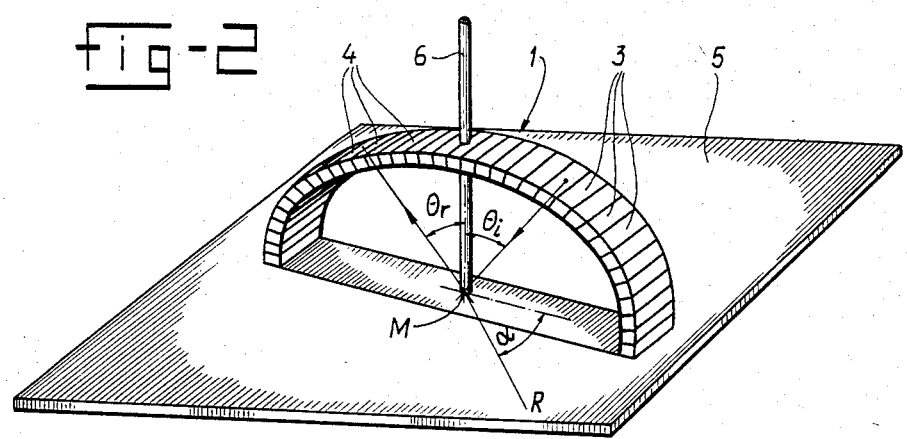
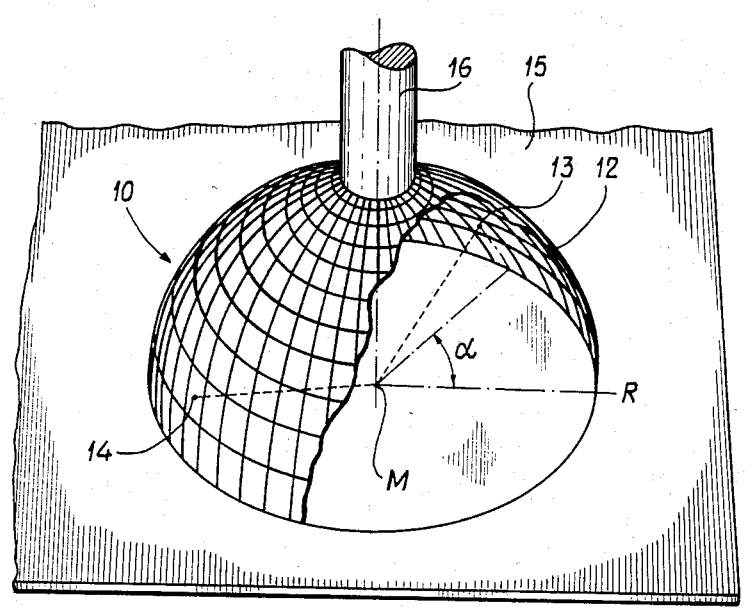

METHOD AND APPARATUS FOR THE NON-DESTRUCTIVE TESTING OF MATERIALS BY THE USE OF ULTRA-SONIC WAVES

The invention relates to a method for non-destructive, qualitative testing of properties of materials, whereby ultra-sonic waves are transmitted in the direction of the material and ultra-sonic waves are received from the material, whereby the orientation of the material relative to the direction in which said ultra-sonic waves are transmitted is changed in a predetermined way such that said transmitted ultra-sonic waves arrive at the material unter varying angles of incidence and from different directions. Furthermore the invention relates to devices for executing said method.

Such a method is known from the article "Measurement of the elastic constants of fibre composites by ultrasonics" published in Composites, March 1970, pp. 145-149. For this method a sheet of the material to be tested is attached to a turntable and two ultra-sonic transducers are positioned at both sides of the sheet, one being used as transmitter and the other as receiver. This entire combination comprising turntable, transmitter and receiver is placed in a tank, which is filled with a suitable liquid, for instance water, said liquid permits transmission of longitudinal waves from said one transducer to the other. Subsequently pulses are transmitted by the transmitted transducer at a plurality of varying angles of incidence and varying directions of incidence of the waves arriving at the sheet, said waves propagate through the sheet and through the liquid from the transmittor to the receiver.

If the waves enter the sheet perpendicular said entering wave will propagate through the sheet as longitudinal wave. The time of arrival of this pulse at the receiver is measured by a digital time measuring system. If the sheet is now turned by the turntable such that the angle of incidence gradually increases, the entering wave will be divided in the sheet in two components, a pseudo-longitudinal component and a pseudo-transversal component. Both wave components propagate through the sheet and will reach the receiver at different points of time. Based on the measured time differences it is now possible to determine the speed of propagation of the waves in the sheet to be tested.

Departing from said method it is now further possible to determine fibre directions in laminated composite and fibre reinforced materials, as described in "Nondestructive Composite Laminate Characterization by Means of Ultrasonic Polar-Scan" published in Materials Evaluation, vol. 39, no. 10 pp. 922-925. In this method the test sheet is rotated about two mutual perpendicular axes, while the transmitter and the receiver are on a third axis, perpendicular to said both other axes. The signals supplied to the stepping motors for rotating the sheet about both first mentioned axes, are also supplied to an oscilloscope for locating the spot on the screen of the oscilloscope. The signal provided by the receiver in response to the reception of a ultra-sonic pulse, is used for modulating the brightness of the spot on the display screen.

In this way so-called polar diagrams can be recorded for instance for fibre reinforced materials (fibre reinforced epoxy resins etc.) from the screen, which polar diagrams provide information about the fibre direction in the tested material as is described in the above mentioned article.

Said method has a number of drawbacks. From the material to be tested a special test sheet has to be made, which is secured to the turntable in the liquid tank after which the above described measurement can be carried out, resulting in a polar diagram. Because the transmitter and the receiver have to be positioned at both sides of the test sheet and because the test sheet has to be positioned in a liquid tank this method cannot be used with larger sheet materials or constructions built from fibre reinforced epoxy resin material.

A further draw back is the rather complex construction of the device for carrying out said method, because of the simultaneous rotation about two mutual perpendicular axes.

An object of the invention is not to provide a method in which said mentioned drawbacks are eliminated.

This object is met by a method of the kind described in the preamble, in which the ultra-sonic waves reflected by the material are received. This implies that according to the invention both the transmitter and the receiver are positioned at the same side of the material such that ultra-sonic pulses are transmitted by the transmitter in the direction of the material whereas the receiver receives the ultra-sonic pulses reflected by this material. As both transmitter and receiver are at the same side of the material, no separate test sheet has to be made and also measurements can be done at larger sheets of material to be tested and also at structures made from the material to be tested, for instance airplane wings or parts of it or other parts of airplane structures, car body parts and other structures in which fibre reinforced materials can be used.

According to a preferred embodiment of the method according to the invention waves, reflected by the material are received at a number of places at or adjacent to the direction of reflection. In that case it is possible to determine exactly the optimum in the reflected wave and the associated direction of reflection when the angle of reflection is varying.

According to a preferred method several transmitters respectively several receivers are used for transmitting respectively receiving ultra-sonic waves, which are positioned on a spherical-surface of which the center coincides with the point of incidence of the ultra-sonic waves on the material to be tested, whereby each time one transmitter and the associated receiver(s) are activated such that both the angle of incident of the ultra-sonic waves on the material and the direction of incidence of the ultra-sonic waves are varied in a predetermined way. Thereby it is assured uner all circumstances that the propagation path of the ultra-sonic waves between the transmitter and the receiver has the same length, so that the measurement cannot not be influenced by differences in propagation time.

A device for carrying out said method, which device is provided with means for transmitting ultra-sonic waves, means for receiving said ultra-sonic waves and means for positioning said transmitting means and receiving means relative to the material to be tested, is according to the invention characterized in that said means for transmitting and receiving the ultra-sonic waves comprise a plurality respective of transmitters and receivers respectively, for ultra-sonic waves and that said means for positioning said transmitters and receivers comprise a holder to be placed at one side of the material to be tested, which holder supports both the transmitters and the receivers relative to the material to be tested, whereby the transmitters and receivers are directed to the point of incidence of the ultra-sonic waves on the material and the transmitters and receivers are positioned in a plane through said rotation axis equally spaced distance from said point of incidence said holder further being connected with means for rotating said holder above the surface of the material to be tested about a rotation axis, which extends perpendicular to the material through the point of incidence of the ultra-sonic waves on the material.

Preferably the transmitters are positioned on one half of the holder such that the whole range of angles of incidence being of interest is covered step by step. The receivers are distributed in the same way onto the other half of the holder. When performing a revolution measurement values will be simultaneously obtained along a plurality of circular paths, such that after one revolution all measurement value's necessary for constructing the polar diagram are scanned.

According to a further embodiment the holder is provided with guiding means for guiding the transmitters and receivers in the related plane through the rotation-axis, along a semi circular path, of which the center during use of the device coincides with the desired point of incidence of the ultra-sonic waves on the material, and is provided with drive means for moving the transmitters and receivers along the related semi-circular path. Preferably these drive means are energized for stepwise displacing the transmitters and receivers along the guiding means over a predetermined distance after executing a complete revolution about the rotation-axis.

It will be clear that by suitably controlling the drive means related to the controlling of the rotation means, the entire desired polar diagram can be recorded in a continuous measuring process and can for instance made visible on a display screen. This is however supposed to be known for the one skilled in the art and will not be discussed in detail.

The means for moving the transmitter(s) and receiver(s) along the guiding means can be completely omitted if the holder comprises a semi spherical guiding surface, of which the center during use coincides with the point of incidence of the ultra-sonic waves on the material, said semi-spherical guiding surface being rotatable about the rotation-axis perpendicular to the material through the point of incidence of the ultra-sonic waves on the material and on which semi-spherical guiding surface the transmitter and receiver of each couple can be positioned. This embodiment has the further advantage that the positioning of the measuring instrument, in particular the positioning of the semi-spherical holder on the material to be tested, does provide much problems, because it is only necessary to position the edge of the semi-spheral holder onto the material to be tested after which the device is ready for use.

To completely eliminate any movements of the holder, respectively of the convertors on this holder, a third preferred embodiment of the invention is characterized in that the semi-spherical guiding surface itself stands still relative to the material during use and that a plurality of transmitters and receivers is positioned onto this surface distributed over the surface in a predetermined way.

Further advantages and details of the invention will become clear from to the following discussion with reference to the figures which only schematically show embodiments.

FIG. 2 shows a further development of the holder according to FIG. 1, onto the semi-circular surface of which a plurality of transmitters and receivers is placed.

FIG. 3 shows an embodiment of the holder in which a plurality of transmitters and receivers is placed on a semi-spherical surface.

Figure 1:
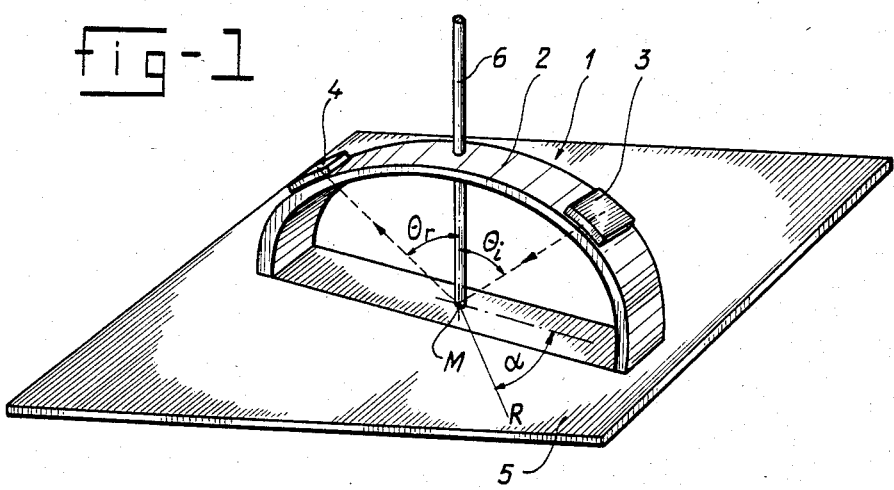
FIG. 1 shows the principle of the invention by means of a schematically shown embodiment, in which the holder is provided with a semi-circular surface on which one single transmitter and one single receiver are mounted.

FIG. 1 shows schematically in perspective view a device for carrying out the method according to the invention. This device is provided with a holder 1 having a semi-circular surface 2, on which two ultra-sonic convertors 3 and 4 are secured. Both convertors are placed such that their active transmitting or receiving surface is faced to the center M of the semi-circular surface 2. As shown with arrows in the figure convertor 3 is used as transmitter, transmitting ultra-sonic pulses in the direction of the sheet material 5 to be tested. The holder 1 is placed in a position against the sheet material 5, such that the point M coincides which the surface of the sheet material 5. Ultra-sonic pulses, transmitted by transmitter 3, will hit the sheet material 5 in point M and from there pulses will be reflected in the direction of receiver 4. The angle of incidence $\Theta_i$ of the entering pulses, measured relative to a line through M perpendicular at the sheet material 5, equals the angle of reflection $\Theta_r$ measured in the same way and the transmitter 3 and the receiver 4 so are positioned onto the surface 2 symmetrical relative to this perpendicular line through M.

A shaft 6 is secured such to holder 1 such that through rotation of this shaft by means not illustrated drive means holder 1 is rotating about said perpendicular line through M. During this rotation the lower side of holder 1 remains in contact with the surface of the sheet of material 5.

For recording a polar diagram by means of this schematically illustrated device, first the transmitter and the receiver have to be fixed on holder 2 under a first predetermined angle of incidence/reflection $\Theta$ and subsequently the holder is rotated, starting at a arbitrary chosen reference direction R, until an entire revolution is completed. During this revolution transmitter 3 emits ultra-sonic pulses, which are received by receiver 4. The received pulses are evaluated and registered, such that for a given angle of incidence and directions of incidence varying between 0° and 360° relative to the reference direction a plurality of measurement values can be obtained. Thereafter said measuring step is repeated for different angles of incidence until sufficient measurement values are obtained to be able to construct the polar diagram therefrom.

If the device is provided with guiding means for guiding transmitter 3 and receiver 4 along the arc surface 2 and with drive means for moving transmitter 3 and receiver 4 along said guiding means, then polar diagrams can be recorded in a similar way as described in the above mentioned article "Nondestructive Composite Laminate Characterization . . . " by means of an oscilloscope.

It will be clear that such an embodiment, although practically realisable, has a fairly complicated structure.

A mechanical simplification, shown in FIG. 2, is obtained if the arc surface 2 of holder 1' is provided with a plurality of ultra-sonic convertors preferably a joint series, of which one half indicated by 3, acts as a transmitter whereas the other half, indicated by 4 acts as a receiver. In this case both guiding means for guiding the transmitter and receiver along the arc surface 2 of the holder and the drive means for moving the transmitter and the receiver along the guiding means can be omitted.

During rotation of the holder about shaft 6 all transmitters and receivers can in principle be switched on such that after one revolution of the holder all measurement values are recorded. Mutual influencing of various signals is however in that case not only imaginable. To prevent this during one revolution preferably only one transmitter is switched on together with all receivers or a group of receivers, which are positioned near the optimum point for receiving the reflected wave. During a next revolution the next combination of one transmitter and a number of receivers is switched on, and so on. The energizing of the right combination of a transmitter and a group of receivers in the right sequence is controlled by suitable controlling means. The embodiment of this controlling means is supposed to be known to a person skilled in the art.

FIG. 3 shows an embodiment of the device according to the invention in which holder 10 has a semi spherical surface 12, which is provided with a large number of ultra-sonic convertors. As an example in FIG. 3 one transmitting convertor is indicated by 13 and a receiving convertor, which forms the center of a group of receivers which are switched on if this transmitter 13 is energized, has the reference number 14. However, preferable in this embodiment of the device convertors are used which can act both as transmitter as well as receiver. This means that convertor 14 can also transmit signals whereby converter 13 functions as one of the receivers. In that case it is possible to measure all possible directions of incidence varying between 0° and 360° without moving the holder. Electronic control means are used such that each time during a predetermined period a combination of a transmitter and associated receiver are energized for recording a measurement value corresponding with the angle of incidence and the direction of incidence of the related transmitter-receiver couple. In this embodiment of the device no moving parts are necessary anymore. The device is simply placed on the material to be tested and the electronic control means are in fact controlling the measuring procedure. The shaft 16 in this case only acts as a handle or support member to push the holder 15 against the material to be tested.

If the embodiment of FIG. 3 is embodied rotatable about shaft 16 then it is possible to choose different positions for the convertors onto various intersectional lines of the spherical surface with various planes through the rotation-axis. Viewed in the rotational direction preferably the convertors on one intersectional line are shifted relative to the convertors on the adjacent lines, over a distance corresponding to a part of the center to center distance between two convertors on one and the same intersectional line. Thereby the number of circles, corresponding with the number of angles of incidence can be extended considerably. It at each intersectional line m transmitting and m receiving convertors are provided and if there are n intersectional lines at which these convertors are positioned in a shifted configuration, then in this way measuring values from m x n different angles of incidence can be obtained.

I claim:

1. A method for the non-destructive, qualitative testing of the properties of materials by the use of ultrasonic waves, comprising the steps of:
    a. transmitting ultrasonic waves towards the material to be tested at varying angles of incidence and from different directions by means of a plurality of transmitters;
    b. receiving the transmitted waves reflected by the material by means of a plurality of receivers; and
    c. varying the angle and direction of incidence of the ultrasonic waves by activating the transmitters and receivers in a predetermined way;
    said transmitters and receivers being positioned in a semi-spherical arrangement relative to the material, the center of said semi-spherical arrangement coinciding with the point of incidence of the ultrasonic waves on the material to be tested.

2. The method according to claim 1, wherein ultrasonic transducers are substituted for the transmitters and receivers.

3. An apparatus for the non-destructive, qualitative testing of the properties of materials by the use of ultrasonic waves, comprising:
    a. a plurality of transmitters for the transmission of ultrasonic waves towards the material to be tested;
    b. a plurality of receivers for the reception of the transmitted waves reflected by the material to be tested;
    c. a semi-spherical support, relative to the material to be tested; upon which the transmitters and receivers are positioned in a manner to transmit ultrasonic waves to a point of incidence on the material to be tested and to receive the reflected waves from the point of incidence thereof, the point of incidence of ultrasonic waves on the material coinciding with the center of said semi-spherical support; and
    d. a shaft secured perpendicularly to the center of said support.

4. The apparatus of claim 3, which additionally comprises an electronic control means for activating the transmitters and receivers in a predetermined way.

5. The apparatus of claim 3, wherein ultrasonic transducers are substituted for the transmitters and receivers.

* * * * *